(12) United States Patent
Bender et al.

(10) Patent No.: US 7,727,245 B2
(45) Date of Patent: Jun. 1, 2010

(54) METHOD FOR CLOSING AN OPENING IN TISSUE WITH A SPLAYABLE STAPLE

(75) Inventors: Theodore M. Bender, San Francisco, CA (US); Zachary Warder-Gabaldon, Palo Alto, CA (US); Matthew B. Newell, Portola Valley, CA (US); Bernard A. Hausen, Menlo Park, CA (US); Brian R. DuBois, Redwood City, CA (US); Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 240 days.

(21) Appl. No.: 12/013,334

(22) Filed: Jan. 11, 2008

(65) Prior Publication Data

US 2008/0114397 A1    May 15, 2008

Related U.S. Application Data

(62) Division of application No. 11/093,003, filed on Mar. 28, 2005, now Pat. No. 7,344,544.

(51) Int. Cl.
*A61B 17/10* (2006.01)
(52) U.S. Cl. .................................................. 606/139
(58) Field of Classification Search ............... 606/139, 606/153; 623/23.72; 227/175.1, 176.1, 19
See application file for complete search history.

(56) References Cited

U.S. PATENT DOCUMENTS 3,526,228 A    9/1970    Lyng 3,958,576 A    5/1976    Komiya
4,317,451 A    3/1982    Cerwin et al.

(Continued)

FOREIGN PATENT DOCUMENTS

WO    WO-99/62408    12/1999

(Continued)

OTHER PUBLICATIONS

*Notification of Transmittal of the International Search Report and the Written Opinion of the International Searching Authority.*

(Continued)

*Primary Examiner*—Darwin P Erezo
*Assistant Examiner*—Gregory Anderson
(74) *Attorney, Agent, or Firm*—Brian A. Schar

(57) ABSTRACT

One method for closing an opening in tissue may include providing a substantially continuous solid staple having a plurality of tines and a longitudinal centerline, plastically deforming the staple to a splayed configuration; penetrating at least one tine into tissue in proximity to the opening; and plastically deforming the staple to a closed configuration. Another method for closing an opening in tissue may include providing a staple having a plurality of tines; plastically deforming the staple to a splayed configuration by applying force in the distal direction against a proximal surface of the staple; penetrating at least one tine into tissue in proximity to the opening; and plastically deforming the staple from the splayed configuration to a closed configuration by applying force in the distal direction against a proximal surface of the staple.

15 Claims, 12 Drawing Sheets

U.S. PATENT DOCUMENTS

| | | | |
|---|---|---|---|
| 4,509,518 A | 4/1985 | McGarry et al. |
| 4,836,204 A | 6/1989 | Landymore et al. |
| 5,007,921 A | 4/1991 | Brown |
| 5,026,390 A | 6/1991 | Brown |
| 5,042,707 A | 8/1991 | Taheri |
| 5,156,609 A | 10/1992 | Nakao et al. |
| 5,201,745 A | 4/1993 | Tayot et al. |
| 5,411,523 A | 5/1995 | Goble |
| 5,413,584 A | 5/1995 | Schulze |
| 5,591,177 A | 1/1997 | Lehrer |
| 5,662,681 A | 9/1997 | Nash et al. |
| 5,674,231 A | 10/1997 | Green et al. |
| 5,695,504 A | 12/1997 | Gifford, III et al. |
| 5,728,109 A | 3/1998 | Schulze et al. |
| 5,792,094 A | 8/1998 | Stevens et al. |
| 5,810,846 A | 9/1998 | Virnich et al. |
| 5,843,124 A | 12/1998 | Hammerslag |
| 5,861,005 A | 1/1999 | Kontos |
| 5,910,155 A | 6/1999 | Ratcliff et al. |
| 6,022,372 A | 2/2000 | Kontos |
| 6,042,584 A | 3/2000 | Pierson, III |
| 6,149,660 A | 11/2000 | Laufer et al. |
| 6,197,042 B1 | 3/2001 | Ginn et al. |
| 6,269,819 B1 | 8/2001 | Oz et al. |
| 6,277,140 B2 | 8/2001 | Ginn et al. |
| 6,302,898 B1 | 10/2001 | Edwards et al. |
| 6,322,580 B1 | 11/2001 | Kanner |
| 6,348,064 B1 | 2/2002 | Kanner |
| 6,355,050 B1 | 3/2002 | Andreas et al. |
| 6,368,341 B1 | 4/2002 | Abrahamson |
| 6,371,974 B1 | 4/2002 | Brenneman et al. |
| 6,391,048 B1 | 5/2002 | Ginn et al. |
| 6,451,031 B1 | 9/2002 | Kontos |
| 6,461,364 B1 | 10/2002 | Ginn et al. |
| 6,482,224 B1 | 11/2002 | Michler et al. |
| 6,506,210 B1 | 1/2003 | Kanner |
| 6,508,828 B1 | 1/2003 | Akerfeldt et al. |
| 6,524,321 B2 | 2/2003 | Kanesaka |
| 6,524,326 B1 | 2/2003 | Zhu et al. |
| 6,533,762 B2 * | 3/2003 | Kanner et al. ............... 604/175 |
| 6,540,735 B1 | 4/2003 | Ashby et al. |
| 6,623,510 B2 | 9/2003 | Carley et al. |
| 6,626,918 B1 | 9/2003 | Ginn et al. |
| 6,632,238 B2 | 10/2003 | Ginn et al. |
| 6,676,685 B2 | 1/2004 | Pedros et al. |
| 6,695,867 B2 | 2/2004 | Ginn et al. |
| 6,712,828 B2 | 3/2004 | Schraft et al. |
| 6,719,777 B2 | 4/2004 | Ginn et al. |
| 6,726,704 B1 | 4/2004 | Loshakove et al. |
| 6,743,239 B1 | 6/2004 | Kuehn et al. |
| 6,743,248 B2 | 6/2004 | Edwards et al. |
| 6,749,621 B2 | 6/2004 | Pantages et al. |
| 6,755,842 B2 | 6/2004 | Kanner et al. |
| 6,767,356 B2 | 7/2004 | Kanner et al. |
| 6,780,197 B2 | 8/2004 | Roe et al. |
| 6,942,674 B2 | 9/2005 | Belef |
| 2001/0007077 A1 | 7/2001 | Ginn et al. |
| 2001/0021855 A1 | 9/2001 | Levinson |
| 2001/0021856 A1 | 9/2001 | Bolduc et al. |
| 2001/0023352 A1 | 9/2001 | Gordon et al. |
| 2002/0072768 A1 | 6/2002 | Ginn |
| 2002/0082641 A1 | 6/2002 | Ginn et al. |
| 2002/0133193 A1 | 9/2002 | Ginn et al. |
| 2002/0151921 A1 | 10/2002 | Kanner |
| 2002/0156495 A1 | 10/2002 | Brenneman et al. |
| 2002/0193808 A1 | 12/2002 | Belef et al. |
| 2003/0078598 A1 | 4/2003 | Ginn et al. |
| 2003/0097140 A1 | 5/2003 | Kanner |
| 2003/0100920 A1 | 5/2003 | Akin et al. |
| 2003/0109890 A1 | 6/2003 | Kanner et al. |
| 2003/0158577 A1 | 8/2003 | Ginn et al. |
| 2003/0158578 A1 | 8/2003 | Pantages et al. |
| 2004/0002681 A1 | 1/2004 | McGuckin, Jr. et al. |
| 2004/0010285 A1 | 1/2004 | Carley et al. |
| 2004/0059375 A1 | 3/2004 | Ginn et al. |
| 2004/0073236 A1 | 4/2004 | Carley et al. |
| 2004/0073255 A1 | 4/2004 | Ginn et al. |
| 2004/0092965 A1 | 5/2004 | Parihar |
| 2004/0153122 A1 | 8/2004 | Palermo |
| 2004/0153123 A1 | 8/2004 | Palermo et al. |
| 2004/0176798 A1 | 9/2004 | Epstein et al. |
| 2004/0225301 A1 | 11/2004 | Roop et al. |
| 2005/0021054 A1 | 1/2005 | Ainsworth et al. |
| 2005/0080435 A1 | 4/2005 | Smith et al. |
| 2005/0090834 A1 | 4/2005 | Chiang et al. |
| 2005/0090843 A1 | 4/2005 | Bolduc |
| 2005/0131460 A1 | 6/2005 | Gifford, III et al. |
| 2005/0171561 A1 | 8/2005 | Songer et al. |
| 2005/0187613 A1 | 8/2005 | Bolduc et al. |
| 2006/0200197 A1 | 9/2006 | Brenzel et al. |
| 2007/0010854 A1 | 1/2007 | Cummins |
| 2008/0177300 A1 * | 7/2008 | Mas et al. ............... 606/219 |

FOREIGN PATENT DOCUMENTS

| | | |
|---|---|---|
| WO | WO-00/07640 | 2/2000 |
| WO | WO-00/56223 | 9/2000 |
| WO | WO-00/56227 | 9/2000 |

OTHER PUBLICATIONS

*International Search Report.*
*Written Opinion of the International Searching Authority.*
"Closure and Assisted-Compression Device Update", *Endovascular Today* Apr. 2004, 22.
"Summary of Safety and Effectiveness Data (EVS (TM) Vascular Closure System)", Nov. 3, 2004.
"The EVS(TM) Vascular Closure System by Angiolink", *Business Briefing: US Cardiology 2004* 2004.
"VasoStasis (TM) Vascular Closure System 510(k) Notification", Oct. 22, 2004.

* cited by examiner

US 7,727,245 B2

METHOD FOR CLOSING AN OPENING IN TISSUE WITH A SPLAYABLE STAPLE

FIELD OF THE INVENTION

The present invention relates generally to a system for closing an opening in a hollow tissue structure such as the femoral artery.

BACKGROUND

Millions of people each year undergo catheterization for reasons including stent placement, angioplasty, angiography, atrial ablation, placement of abdominal aortic aneurysm grafts and/or stents, and other interventional cardiologic and vascular procedures. In a femoral artery catheterization, an opening is made in the wall of the femoral artery, and a sheath is placed in that opening through which a guidewire and one or more tools may be inserted for performing treatment on the patient.

After the sheath is removed, the opening in the femoral artery must be closed. Compression is typically used to do so. Anticoagulation therapy is stopped, and manual pressure is applied to the site for up to an hour until clotting seals the access site. The patient then must remain motionless for up to 24 hours, generally with a sandbag or other heavy weight on the site to continue the compression. Many patients find this procedure, and the resultant bruising and pain, to be more unpleasant than the actual interventional procedure that was performed.

Several types of closure devices and techniques have been developed in an attempt to facilitate closure of the opening in the femoral artery. However, acceptance of these devices and techniques has been limited for several reasons, including complexity of use, complication rates similar to traditional closure, and cost. One type of device utilizes suture to close the opening. However, such devices are typically complex mechanically and consequently are complex to operate. Further, such devices often require an auxiliary knot-pushing tool to be used, further increasing complexity. Other devices are ring-shaped or shaped in a convoluted or tortuous manner, and are complicated and expensive to manufacture. Another closure technique involves inserting a plug or slurry of collagen or other chemical composition into the opening and/or the pathway in the leg between the opening and the skin. However, compression and lengthy bed rest are generally still required with chemical closure techniques, just as with traditional closure.

BRIEF DESCRIPTION OF THE DRAWINGS

The use of the same reference symbols in different figures indicates similar or identical items.

DETAILED DESCRIPTION

Closure System

Figure 1:
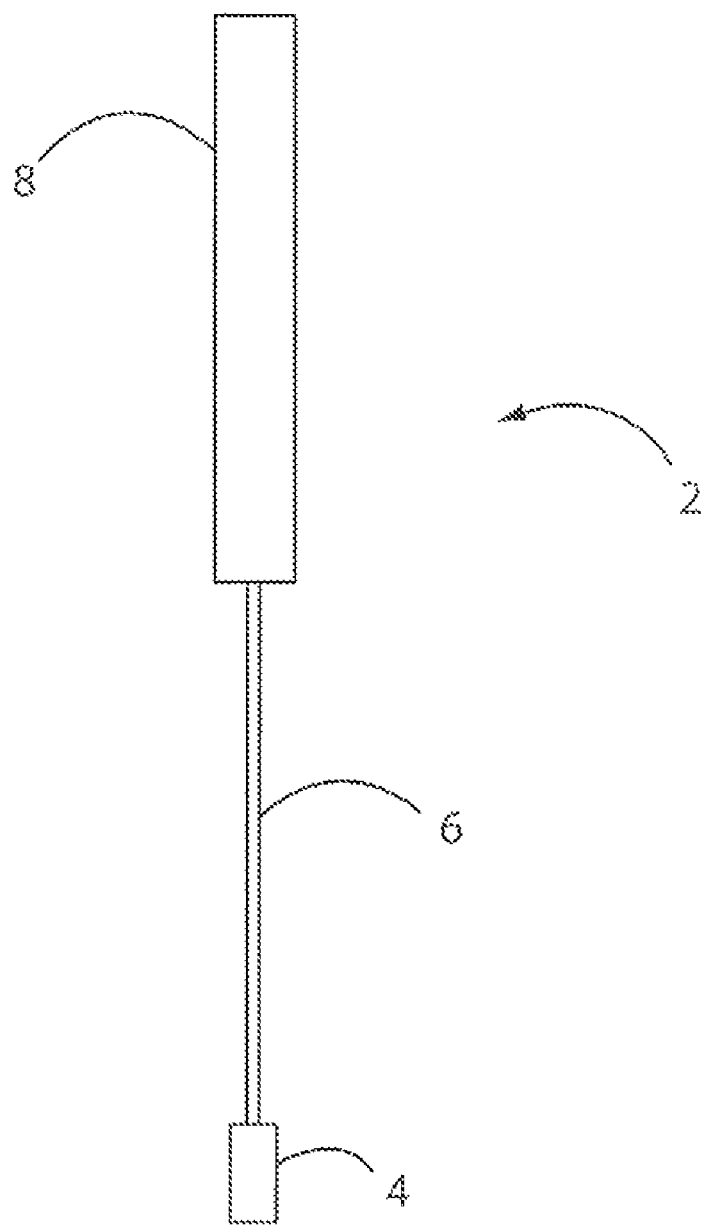
FIG. 1 is a schematic view of a vascular closure system that includes an end effector, a shaft and a handle.
Figure 7:
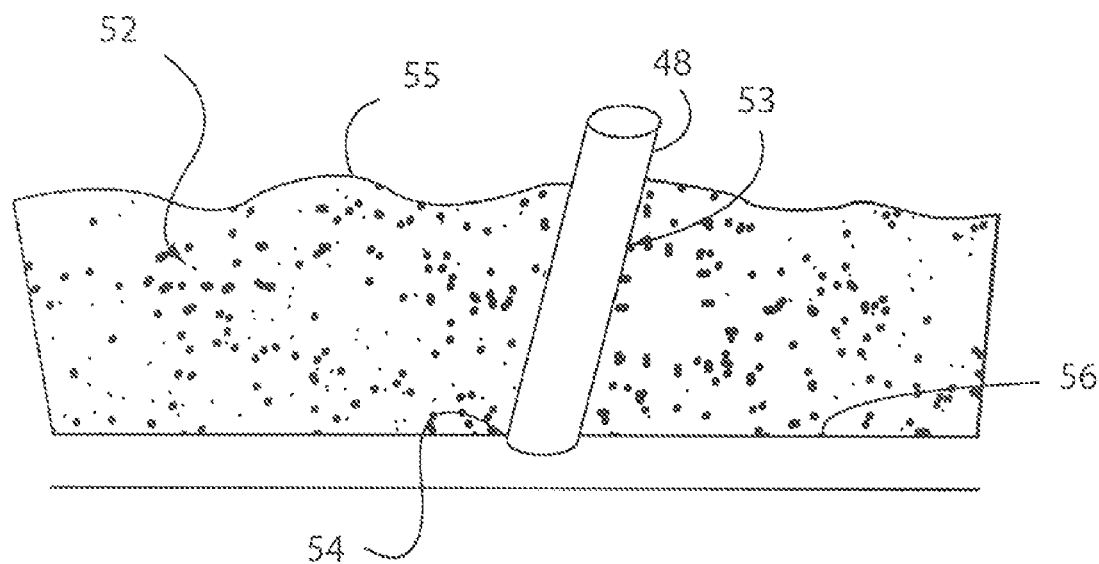
FIG. 7 is a schematic view of tissue having a catheterization sheath positioned therein.

Referring to FIG. 1, a closure system 2 includes an end effector 4 connected to a shaft 6, which in turn is connected to a handle 8. The end effector 4 may be one or more separate components that are connected to the shaft 6, or may be fabricated integrally with the distal end of the shaft 6. Referring also to FIG. 7, the end effector 4 is sized to pass through a standard sheath 48 placed in a passage 53 in tissue 52 for a standard catheterization procedure.

Figure 2:
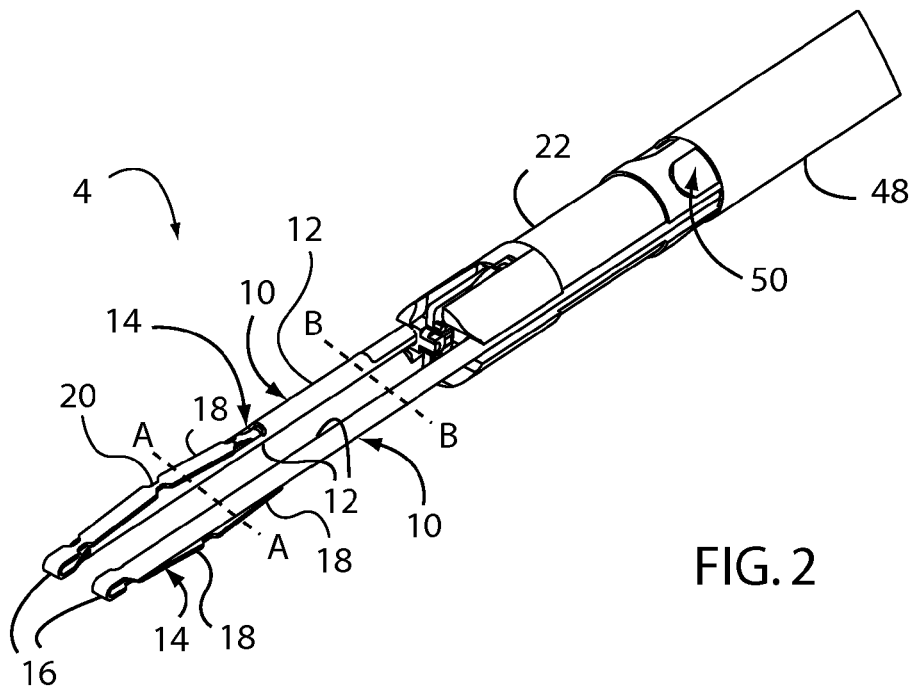
FIG. 2 is a perspective view of the end effector having butterfly members in a first, collapsed configuration.
Figure 3A:
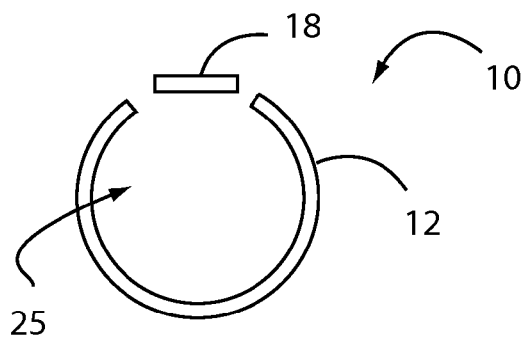
FIG. 3A is a cross-section view of a butterfly member of the end effector along the line A-A in FIG. 2.
Figure 3B:
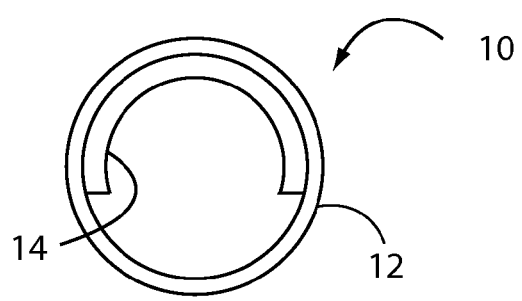
FIG. 3B is a cross-section view of a butterfly member of the end effector along the line B-B in FIG. 2.

Referring also to FIG. 2, the end effector 4 includes at least one butterfly member 10. Each butterfly member 10 acts to register tissue such as the wall of a blood vessel to the end effector 4, as described in greater detail below. At least one butterfly member 10 may extend substantially distally from a housing 22 or other component of the end effector 4. Alternately, at least one butterfly member 10 extends at least partially in a different direction. Each butterfly member 10 may be configured in any manner that allows it to move from a first, collapsed configuration to a second, expanded configuration, and back to the collapsed configuration. As one example, at least one butterfly member 10 includes a first element 12, and a second element 14 connected to the distal end of the first element 12. The first element 12 is not substantially deformable, and at least part of the second element 14 is deformable to an expanded configuration. Alternately, either or both of the elements 12, 14 is deformable to an expanded configuration. The elements 12, 14 may be shaped and configured in any suitable manner. As one example, referring also to FIGS. 3a-3b, the first element 12 may have a semicircular cross-section or other curved cross-section along at least part of its length. Such a cross section increases the moment of inertia of the first element 12 and thereby increases its stiffness. At least part of the first element 12 may be partially tubular, hollow, or otherwise include an area configured to receive a portion of the second element 14, or vice versa. At least part of the first element 12 may be substantially coaxial with the second element 14. The distal end 16 of at least one butterfly member 10 may be blunt in order to prevent or minimize any disturbance to the tissue structure into which the butterfly member 10 is inserted. For example, the distal end of at least one butterfly member 10 may be curved at the junction between the elements 12, 14. At least one butterfly member 10 may have a longitudinal axis in the collapsed configuration that is offset from and substantially parallel to the longitudinal axis of the end effector 4 and/or the shaft 6. The use of the term "axis" in this document is not limited to use with respect to structures that are cylindrical or radially symmetrical, and the use of the term "axis" in conjunction with a structure does not and cannot limit the shape of that structure. Alternately, at least one butterfly member 10 is oriented differently relative to the longitudinal axis of the end effector 4 and/or the shaft 6.

Figure 13A:
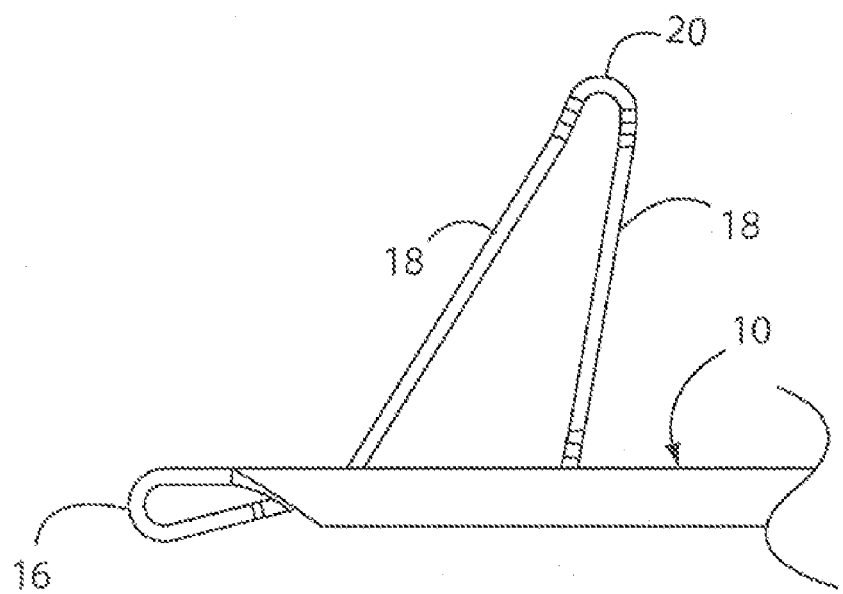
FIG. 13A is a side view of the distal end of one exemplary butterfly member.
Figure 13B:
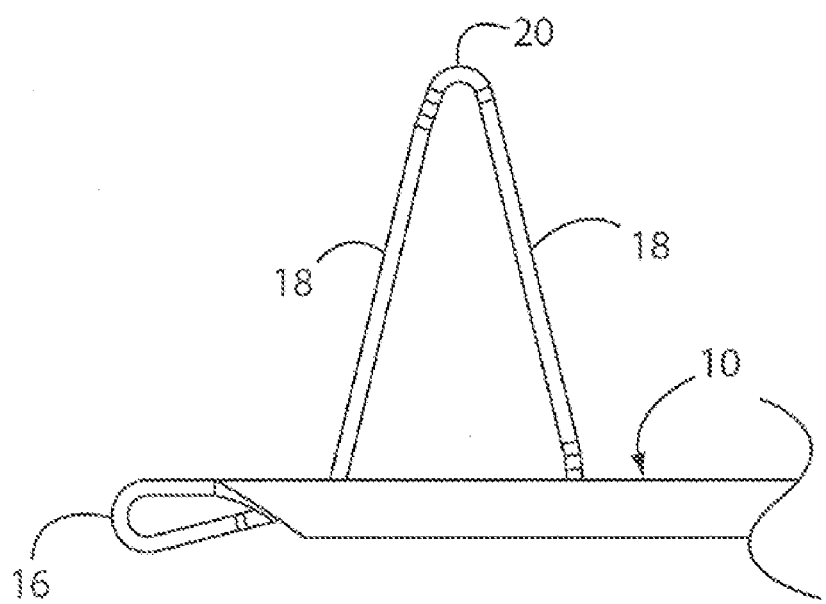
FIG. 13B is a side view of the distal end of a different exemplary butterfly member.

The second element 14 may include two substantially planar segments 18 longitudinally spaced from one another and connected to one another by a hinge element 20 between them, such that one segment 18 is positioned distal to the other segment. The hinge element 20 may be a living hinge, such as a narrower area between the two segments 18 that bends to allow movement between the segments 18. Alternately, the hinge element 20 may be any structure or mechanism that allows for relative movement between the segments 18. At least one of the segments 18 may be curved or otherwise non-planar. One of the planar segments 18 may extend to a location at or in proximity to the distal end 16 of the corresponding butterfly member 10. The segments 18 may be angled relative to one another when the butterfly member 10 is in the first, collapsed configuration. For example, the most-distal segment 18 may be angled relative to the longitudinal axis of the corresponding butterfly member 10 such that the distal end of that segment 18 is closer to that longitudinal axis than the proximal end of that segment 18, and the most-proximal segment 18 may be angled relative to the longitudinal axis of the corresponding butterfly member 10 such that the proximal end of that segment 18 is closer to that longitudinal axis than the distal end of that segment 18. Alternately, the segments 18 may be angled differently relative to one another. The angle between the segments 18 allows the hinge 20 to deform or otherwise move upon application of force to the second element 14, as described in greater detail below. The segments 18 may be angled relative to one another a greater amount when the butterfly member 10 is in the second, expanded configuration than in the first, collapsed configuration. Alternately, the segments 18 may be substantially parallel to one another and/or lie in substantially the same plane as one another. Referring to FIG. 13A, the segments 18 each may be substantially the same length, such that they form a symmetrical shape upon actuation of the butterfly member 10. Alternately, referring to FIG. 13B, the segments 18 may differ in length, such that they form a non-symmetrical shape upon actuation of the butterfly member 10.

Referring also to FIG. 2, the first element 12 may extend into the housing 22 of the end effector 4 through a notch, aperture or other opening. The first element 12 may instead extend along a groove or other receiving area of the housing 22, rather than or in addition to extending into the housing 22. The first element 12 is movable relative to the housing 22. Alternately, the first element 12 is fixed substantially to the housing 22. The first element 12 may extend through the shaft 6 to the handle 8. The proximal end of the first element 12 extends substantially proximally from the housing 22 in any suitable amount.

A proximal portion of the second element 14 may extend into a center area 25 of a proximal portion of the first element 12. That center area 25 of the first element 12 may be referred to as the lumen of the first element 12 for convenience, even though the first element 12 may be open along part of its perimeter, or may have a cross-section other than circular, at any portion of its length. The longitudinal axis of the lumen 25 may be substantially coincident with the longitudinal axis of the first element 12, or may be offset from or otherwise aligned relative to the longitudinal axis of the first element 12. The second element 14 may be movable relative to that lumen 25, such as by sliding substantially along or substantially parallel to the longitudinal axis of the lumen 25. Alternately, the second element 14 does not extend into the lumen 25 of the first element 12. Alternately, the second element 14 does not include a lumen 25. For example, both the first element 12 and the second element 14 may be substantially flat, or gently curved. The elements 12, 14 may be adjacent to one another, or spaced apart from one another, along at least part of their length, particularly where neither element 12, 14 includes a lumen 25. At least one of the elements 12, 14 may be configured to move, such as by sliding, relative to at least part of the other element 12, 14. Alternately, at least part of the second element 14 includes a lumen 25 therein, and a portion of the first element 12 may extend into that lumen 25

The first element 12 and the second element 14 may both be parts of an integral whole, shaped to constitute the butterfly member 10. For example, the butterfly member 10 may be stamped from a sheet of metal, such as stainless steel. The butterfly member 10 may then be folded, where the first element 12 is on one side of the fold and the second element 14 is on the other side of the fold. At least a portion of each member 12, 14 may be folded into a semicircular or other shape as viewed longitudinally, before or after the folding. Each butterfly member 10 may be fabricated from any suitable material. As one example, at least one butterfly member 10 may be fabricated from any material, such as nickel-titanium alloy, that is elastically or superelastically deformable between the first configuration and the second configuration. As another example, at least one butterfly member 10 may be fabricated from any material, such as stainless steel or plastic, that is plastically deformable between the first configuration and the second configuration. At least part of at least one butterfly member 10 may be plastically deformable between the collapsed configuration and the expanded configuration. At least part of the butterfly member 10 may be annealed, such that it can be plastically deformed without fracturing. Both of the elements 12, 14 may be substantially rigid, such that they are capable of transmitting both compressive and tensile force.

Figure 4:
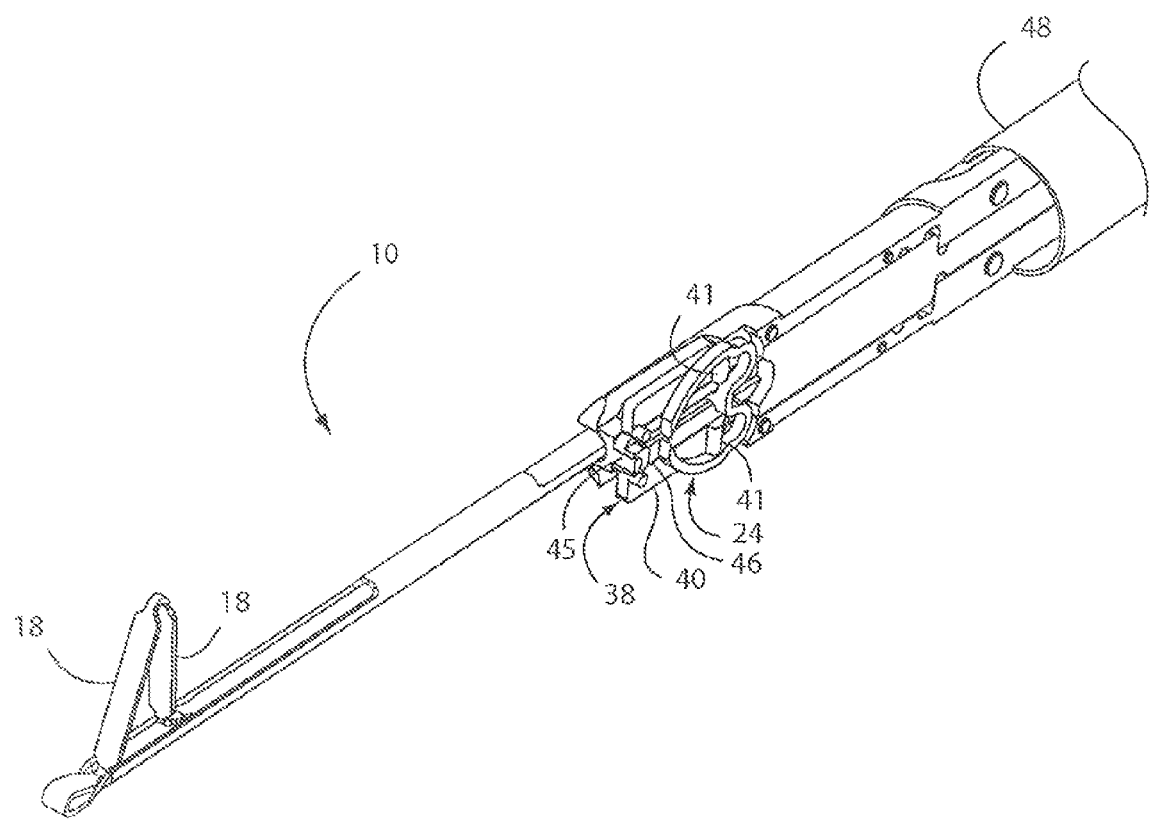
FIG. 4 is a perspective cross-section view of the end effector in a first configuration.
Figure 5:
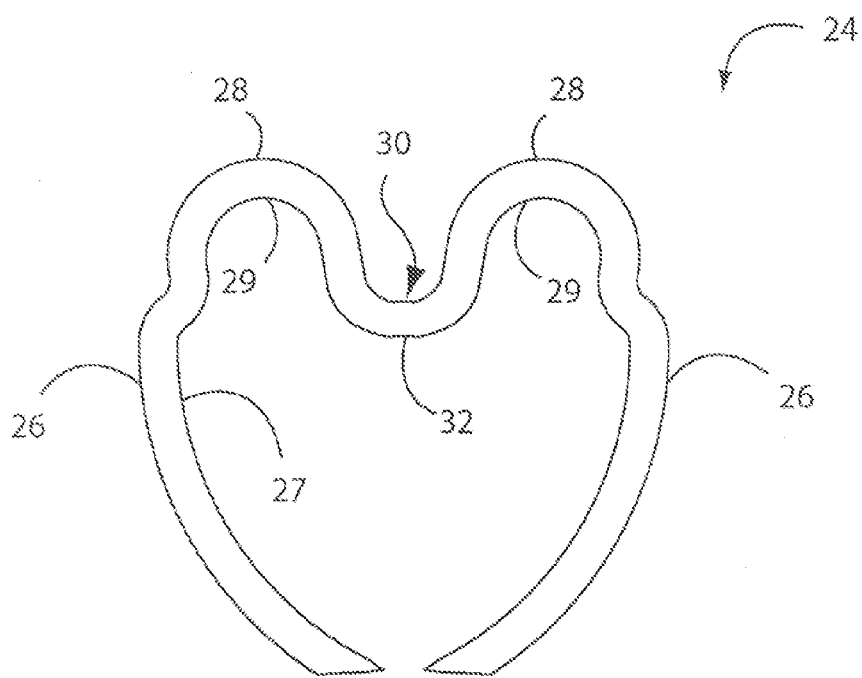
FIG. 5 is a side view of the staple of FIG. 4 in a first configuration.

Referring also to FIG. 4, a staple 24 is initially positioned within a space inside the end effector 4. Alternately, the staple 24 is positioned differently within the end effector 4, or is positioned at the end of the end effector 4 rather than within it. The staple 24 may be sized and shaped in any suitable manner. As one example, referring also to FIG. 5, the staple 24 may have a curved M-shape. However, the staple 24 may have any other suitable shape. The staple 24 may have two tines 26, each extending at least partially in the distal direction. The tines 26 may be curved, and may each have a shape and radius of curvature such that the tines 26 are generally not parallel to one another. The radius of curvature may be substantially coincident with the path of travel of the tines 26 during closure of the staple 24. The staple 24 may be substantially bilaterally symmetrical, although it may be asymmetrical if desired. The staple 24 may be a substantially continuous solid. As used in this document, the term "solid" means that a structure has no slots, holes, apertures or other enclosed or bounded openings defined therein.

The distal end of each tine 26 may have a substantially pointed or sharpened distal end. However, the distal ends of the tines 26 need not be pointed or sharpened, particularly if the cross-sectional area of each tine 26 is small. Advantageously, each tine 26 has a single distal end that is not bifurcated or otherwise forked or split. The body of the staple 24 extends proximally from the distal end of one tine 26 and curves or angles toward the longitudinal centerline of the staple 24. This curve may extend outward from the longitudinal centerline of the staple 24, then toward the longitudinal centerline of the staple 24. Alternately, the tine 26 may curve differently. The body of the staple 24 reaches a peak 28, then extends distally and toward the longitudinal centerline of the staple 24. The body of the staple 24 then reaches a trough 30, then extends proximally and away from the longitudinal centerline of the staple to a second peak 28. The body of the staple 24 continues distally to form the second tine 26, and ends at the distal end of the second tine 26. Alternately, the staple 24 may be shaped differently. For example, the staple 24 may have more than two tines 26. A valley 29 is the area on the staple 24 on the other side of the staple 24 from a peak 28. For example, where a peak 28 of the staple 24 includes a convex curve oriented proximally, the corresponding valley 29 is a concave curve opening distally. Advantageously, the staple 24 is substantially solid.

The staple 24 may include at least one tab 32 extending therefrom in any suitable direction, such as substantially perpendicular to the body of the staple 24. Advantageously, the tab 32 extends from the trough 30 of the staple 24 or from a location in proximity to the trough 30. The staple 24 may include any suitable number of tabs 32. Each tab 32 is sized and positioned to engage a corresponding substantially-longitudinal groove (not shown) in the housing 22. Thus, the tab 32 registers the staple 24 to the housing 22. Alternately, instead of or in addition to a tab 32, the staple 24 may include at least one slot (not shown) that is sized and positioned to engage a corresponding substantially-longitudinal rib (not shown) defined on the housing 22. Alternately, any other structure or mechanism may be used to register the staple 24 to the housing 22.

Figure 12:
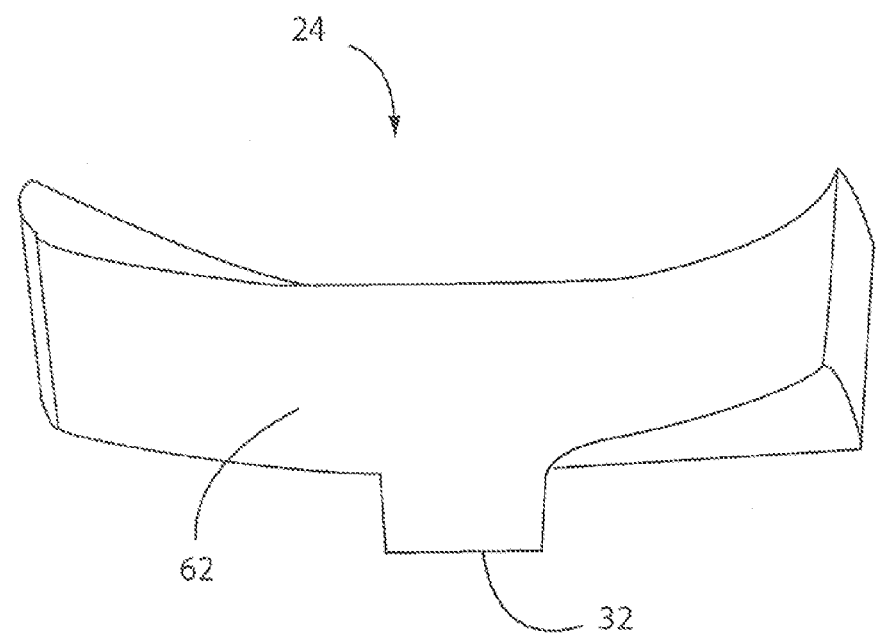
FIG. 12 is a top view of an embodiment of a staple.

The staple 24 may lie substantially in a single plane. That is, the staple 24 is shaped such that a single plane extends through and substantially bisects the entire staple 24. Alternately, the staple 24 does not lie substantially in a single plane. The longitudinal and lateral dimensions of the staple 24 overall may both be substantially larger than the height of the staple 24. Alternately, the staple 24 may be sized differently. Referring also to FIG. 12, the proximal surface 62 of the staple 24 optionally may be curved relative to a plane perpendicular to the longitudinal axis of the staple 24. For example, the proximal surface 62 of the staple 24 may take the shape of a twisted plane. The proximal surface 62 of the staple 24 may be twisted such that a line perpendicular to that proximal surface 62 on one side of the longitudinal centerline of the staple 24 is skewed relative to a line perpendicular to that proximal surface 62 on the other side of the longitudinal centerline of the staple 24, and both such lines are skewed relative to the longitudinal centerline of the staple 24.

The staple 24 may be plastically deformable. If so, the staple 24 may be fabricated from stainless steel, titanium or any other suitable plastically-deformable material. Alternately, the staple 24 may be elastically deformable. If so, the staple 24 may be fabricated from nickel-titanium alloy or any other suitable elastic or superelastic material. The staple 24 may be fabricated from a single wire or other piece of material, having a rectangular, circular or other cross-section. The cross-section of the staple 24 may be substantially constant along the entire staple 24, or may vary at different locations along the staple 24. For example, the cross-sectional area of the staple 24 at certain locations may be less than at other locations, in order to promote bending in those locations having a lesser cross-sectional area.

Figure 10:
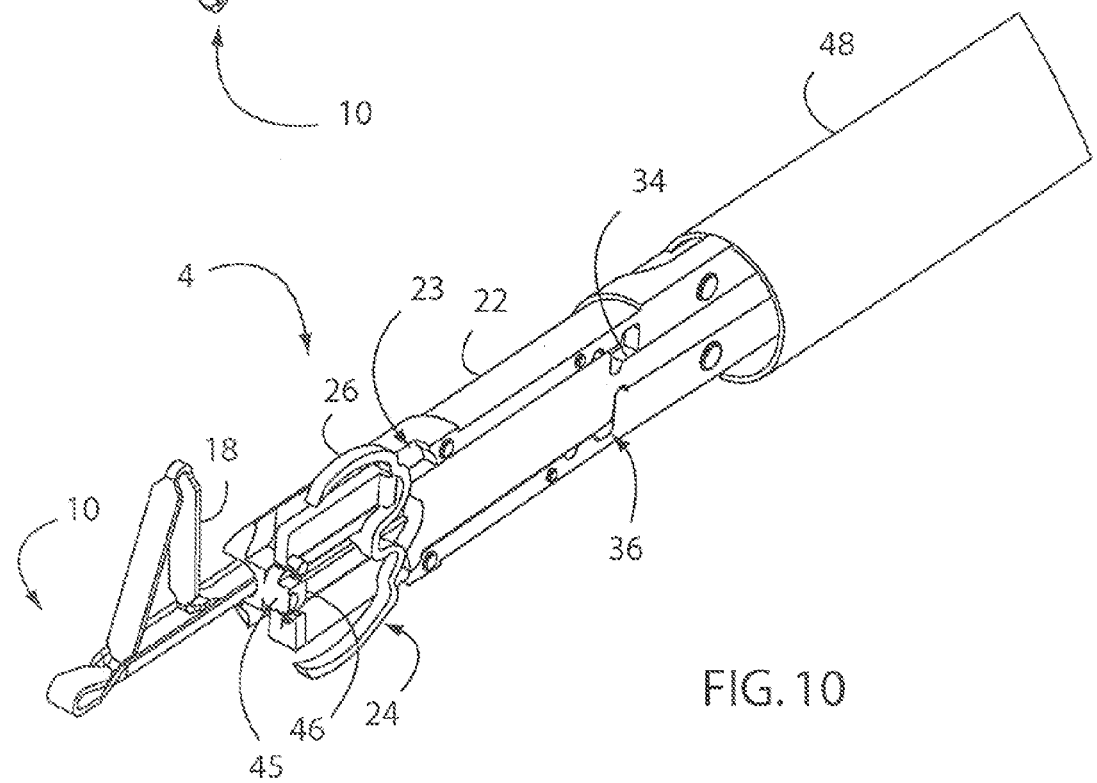
FIG. 10 is a perspective cutaway view of the end effector in a second configuration, as the staple is splayed.

Referring also to FIG. 10, a driver 34 is located proximally to the staple 24, and is movable relative to the staple 24 such as by sliding. At least a portion of the driver 34 may be positioned within the housing 22. The housing 22 may be at least partially hollow in order to accommodate the driver 34. Advantageously, the housing 22 includes a passage 36 therein along which at least part of the driver 34 may slide or otherwise move. At least part of the passage 36 may guide the driver 34 during at least part of its motion. The driver 34 may be configured in any suitable manner. As one example, the driver 34 is an elongated member having a bifurcated distal end, where each bifurcation is configured to engage a corresponding peak 28 of the staple 24. Alternately, the distal end of the driver 34 is shaped differently. The driver 34 may be substantially flat, and may have a thickness substantially equal to that of the staple 24. Alternately, the driver 34 is shaped and/or configured differently, in any suitable manner. Optionally, the staple 24 may be fabricated integrally with the driver 34. If so, the staple 24 is frangible from the driver 34, such that the staple 24 separates from the driver 34 at a suitable time during or after deployment. Fabrication of the staple 24 integrally with the driver 34 may facilitate manufacturing.

Figure 6:
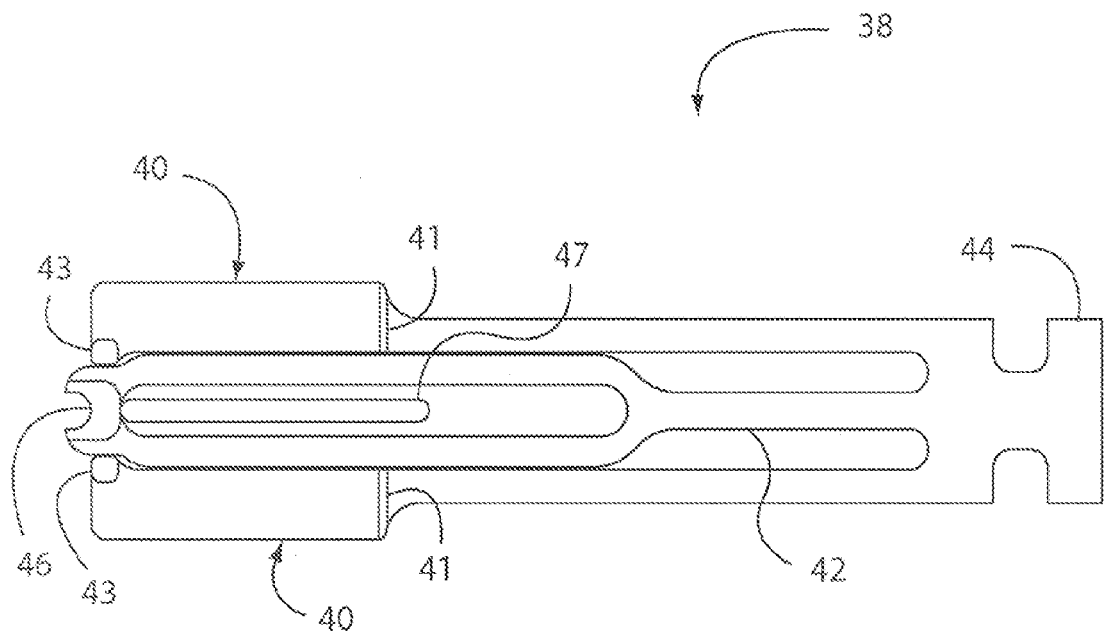
FIG. 6 is a side view of paddles and a finger that are utilized within the end effector.

Referring to FIGS. 4 and 6, a paddle assembly 38 may be located at least partially within the passage 36, at or near the distal end thereof. The paddle assembly 38 may include one or more paddles 40 and/or one or more fingers 42. As one example, two paddles 40 are utilized, and a finger 42 is positioned between the paddles 40, where the paddles 40 and the finger 42 are cantilevered from a base 44 of the paddle assembly 38. At least one paddle 40 may include a ridge 41 raised relative to a remainder of the paddle 40. The ridge 41 may be substantially linear, and may be substantially perpendicular to the longitudinal axis of the paddle 40. The ridge 41 may be shaped as a ramp, with greater thickness at its proximal edge than at its distal edge. The surface of the ramp may be straight, curved or complex. Alternately, the ridge 41 may be a bump, shaped such as a section of a cylinder. Alternately, the ridge 41 may be shaped and/or oriented in any other suitable manner. At least one paddle 40 may include a post 43 at or near its distal end. Each post 43 may be substantially cylindrical. Each post 43 extends from a remainder of the paddle 40, and may be oriented substantially perpendicular to the longitudinal axis of the paddle 40. The finger 42 may be substantially linear, and extend substantially along a plane defined by the base 44 of the paddle assembly 38. The distal end of the finger 42 may extend substantially as far distally as the distal ends of the paddles 40, or may extend distally any other suitable distance. A projection 46 extends from a location at or near the distal end of the finger 42 substantially perpendicular to the longitudinal axis of the finger 42. Alternately, the projection 46 extends in a different direction. When the end effector 4 is in an initial position, the distal end of the driver 34 may be in contact with, or in proximity to, the base 44 of the paddle assembly 38. The projection 46 may include a concave depression or other surface configured to slide along a post 45 extending from the housing 22. The post 45 may guide and/or stabilize the projection 46.

Alternately, the paddle or paddles 40 may be angled or curved relative to the driver 34 such that the driver 34 would contact at least one paddle 40 if the driver 34 moved distally. At least one paddle 40 may be angled or curved toward the staple 24, such that the outer edge of that paddle 40 contacts an inner surface 27 of a tine 26 of the staple 24. That is, the paddle 40 may be angled, curved or otherwise shaped such that at least part of the paddle 40 is positioned between the tines 26 of the staple 24 and is distal to at least part of the staple 24 when the staple 24 is in an initial position. As a result, the paddle or paddles 40 may act both to restrain the staple 24 against distal motion and to hold the staple 24 in its initial configuration.

When the end effector 4 is in the initial position, the staple 24 is also in an initial position. In the initial position, each ridge 41 of each paddle 40 may be positioned distal to a corresponding valley 29 of the staple 24. Further, when the end effector 4 is in the initial position, the distal end of the driver 34 may be positioned against or in proximity the peaks 28 of the staple 24, thereby substantially restraining the staple 24 against motion in the proximal direction. The staple 24 may be held substantially in place while the end effector 4 is in the initial position in any suitable manner. For example, the staple 24 may be gently friction-fit against a portion of the housing 22.

Referring also to FIG. 1, the shaft 6 extends proximally from the end effector 4. The shaft 6 may be flexible or rigid. The shaft 6 may be articulated in at least one location, if desired. Referring also to FIG. 7, the shaft 6 and the end effector 4 are both sized to pass through a standard sheath 48 used in a catheterization procedure. One or more blood leakage indicators 50 may be defined in the shaft 6. At least one blood leakage indicator 50 may be a groove or depression extending along at least part of the length of the shaft 6, and extending distally far enough that the distal end of the blood leakage indicator 50 is distal to the distal end of the sheath 48 when the closure system 2 is in use. Optionally, the shaft 6 may include a cutaway, trough or other feature (not shown) to allow the guidewire (if any) used in the catheterization procedure to remain in place during actuation of the closure system 2. Alternately, the closure system 2 may include or be configured to follow a second guidewire separate from the one utilized to perform a medical procedure.

The handle 8 is connected to the shaft 6, such as to the proximal end of the shaft 6. The shaft 6 may be fabricated such that the handle 8 is simply the proximal end of the shaft 6. Alternately, the shaft 6 and the handle 8 may be two separate items that are connected together in any suitable manner. The handle 8 may include any mechanism, mechanisms, structure or structures configured to actuate the end effector 4. For example, as described later in this document, the handle 8 may be configured to actuate the butterfly members 10 and the driver 34. Thus, any suitable mechanism or mechanisms that are configured to actuate the butterfly members 10 and the driver 34 may be used. A rod (not shown) may be attached to the driver 34, extending through the shaft 6 to the handle 8. The rod may be rigid enough to transmit force distally, and may be flexible enough to move along the shaft 6 where the shaft 6 is flexible. Alternately, a cable may be connected to the driver 34, and that cable may be directed around an axle, nose or other feature (not shown) of the end effector 4 in order to convert proximal motion of the cable to distal motion of the driver 34. Alternately, the driver 34, and/or any other suitable component of the end effector 4, may extend through the shaft 6 to the handle 8, in order to be actuated directly by the handle 8, and may connect directly to a mechanism, mechanisms, structure or structures in the handle 8 configured to actuate the end effector 4. Alternately, a butterfly cable (not shown) may be connected to the proximal end of each butterfly member 10. Each butterfly member 10 may be connected to an individual butterfly cable, or at least two butterfly members 10 may be connected to the same butterfly cable. Each butterfly cable may be connected to either element 12, 14 of at least one corresponding butterfly member 10. Motion of the butterfly cable results in motion of the corresponding element 12, 14.

The handle 8 may also include a source of stored energy for actuating the end effector 4. The source of stored energy may be mechanical (such as a spring), electrical (such as a battery), pneumatic (such as a cylinder of pressurized gas) or any other suitable source of stored energy. The source of stored energy, its regulation, and its use in actuating the end effector 4 may be as described in the U.S. patent application Ser. No. 11/054,265, filed on Feb. 9, 2005, which is herein incorporated by reference in its entirety. The handle 8 may instead, or also, include a connector or connectors suitable for receiving stored energy from an external source, such as a hose connected to a hospital utility source of pressurized gas or of vacuum, or an electrical cord connectable to a power source.

Alternately, the closure system 2 may include at least two separate components: a butterfly deployment tool connected to and configured to place the butterfly members 10, and a staple placement tool which is connected to the end effector 4 and configured to place the staple 24. In this embodiment, the closure system 2 includes two or more separate tools, in contrast to the closure system 2 disclosed above that is a single integrated tool. The staple placement tool may be slidable relative to the butterfly deployment tool, or vice versa. As one example, at least a portion of the butterfly deployment tool may be tubular, and at least a portion of the staple placement tool may be configured to slide within the lumen of the tubular portion of the butterfly deployment tool. As another example, the butterfly deployment tool and/or the staple placement tool may include a groove defined therein, where the other tool includes a rail, rib or other structure configured to slide along that groove. Separating the functions of butterfly deployment and staple placement may facilitate the deployment of multiple staples 24, as described in greater detail below.

Operation

Figure 14:
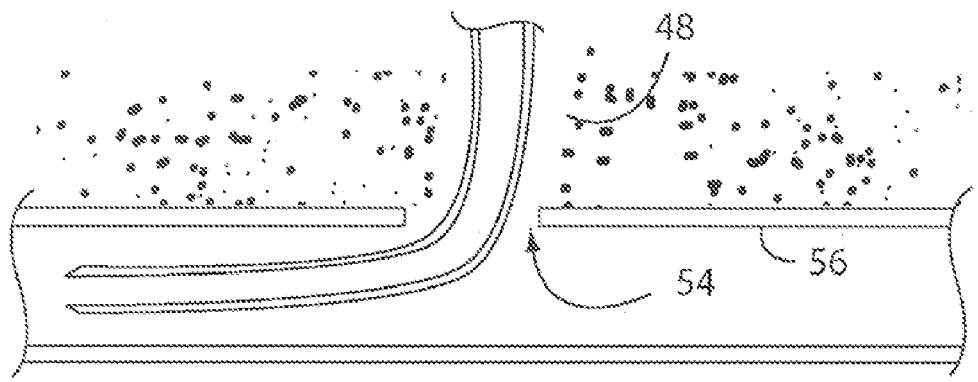
FIG. 14 is a side view of a first step in the operation of the closure system.
Figure 15:
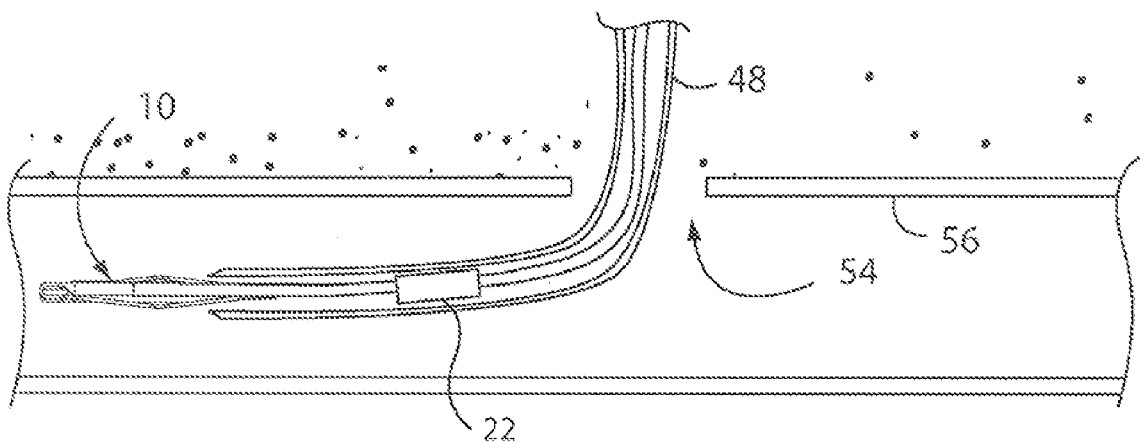
FIG. 15 is a side view of a second step in the operation of the closure system.

Referring to FIGS. 7 and 14, in the course of a standard catheterization procedure, a sheath 48 is inserted through a passage 53 in tissue 52 such that one end of the sheath 48 enters an opening 54 in a blood vessel 56. The passage 53 extends between the epidermis 55 of the patient and the opening 54 in the blood vessel 56. The sheath 48 may be advanced any suitable distance into the blood vessel 56, as determined by the physician performing the procedure. When the sheath 48 is in place, at least one blood leakage indicator 50 is exposed to blood within the blood vessel 56, allowing blood to flow outward therethrough. As an example of a catheterization procedure, the blood vessel 56 may be a femoral artery, and the tissue 52 may be the tissue of the leg between the surface of the leg and the femoral artery. However, the blood vessel 56 may be a different blood vessel, and the tissue 52 may be different tissue in the vicinity of that different blood vessel. During the catheterization procedure, any suitable tools are utilized to perform the desired treatment on the patient, such as the placement of one or more stents in the coronary arteries or peripheral vessels of the patient. After the treatment has been performed, the tools utilized to perform that treatment are removed from the patient via the sheath 48, and the sheath 48 is left in place.

Referring also to FIG. 2, the end effector 4 of the closure system 2 is inserted into the sheath 48. The end effector 4 may be advanced along the sheath 48 in any suitable manner. As one example, the end effector 4 is manually pushed along the sheath 48 by the physician or other user by applying a force to the shaft 6 and/or the handle 8 after the end effector 4 has entered the sheath 48. Each butterfly member 10 initially may be in its first, collapsed configuration as the end effector 4 is advanced along the sheath 48. The end effector 4 continues to advance distally into the sheath 48 until at least the distal end 16 of at least one butterfly member 10 is distal to the distal end of the sheath 48. That is, the end effector 4 is advanced along the sheath 48 until at least the distal end 16 of at least one butterfly member 10 is outside of the lumen of the sheath 48. This position of the end effector 4 relative to the sheath 48 may be referred to as the standby position. The sheath 48 has a known length, and at least part of the end effector 4 is advanced along the lumen of the sheath 48 a distance greater than the length of the sheath 48. Thus, the particular position of the distal end of the sheath 48 in the lumen of the blood vessel 56 need not be known in order for the end effector 4 to be advanced to the standby position. Optionally, one or more markings may be placed on the shaft 6, such that when those one or more markings enter the lumen of the sheath 48, the end effector 4 has been advanced to the standby position. The marking or markings on the shaft 6 are placed at a distance from the distal end of the end effector 4 that is greater than the length of the sheath 48.

Optionally, a guidewire (not shown) utilized in the catheterization procedure may remain in the lumen of the sheath 48, and the end effector 4 and shaft 6 may follow that guidewire in any suitable manner. As one example, where a cutaway, groove or other feature is defined in the end effector 4 and/or shaft 6, that feature may slide along the guidewire. Optionally, the guidewire used in the catheterization procedure is removed from the lumen of the sheath 48 prior to the introduction of the end effector 4 into the sheath 48, and a second, thinner guidewire configured for use with the closure system 2 is inserted through the lumen of the sheath 48 and into the lumen of the blood vessel 56. The original guidewire may be removed before or after the placement of the second guidewire. The second, thinner guidewire, if used, may be more convenient to remove from the opening 54 in the blood vessel 56 after the staple 24 has been closed.

Figure 8:
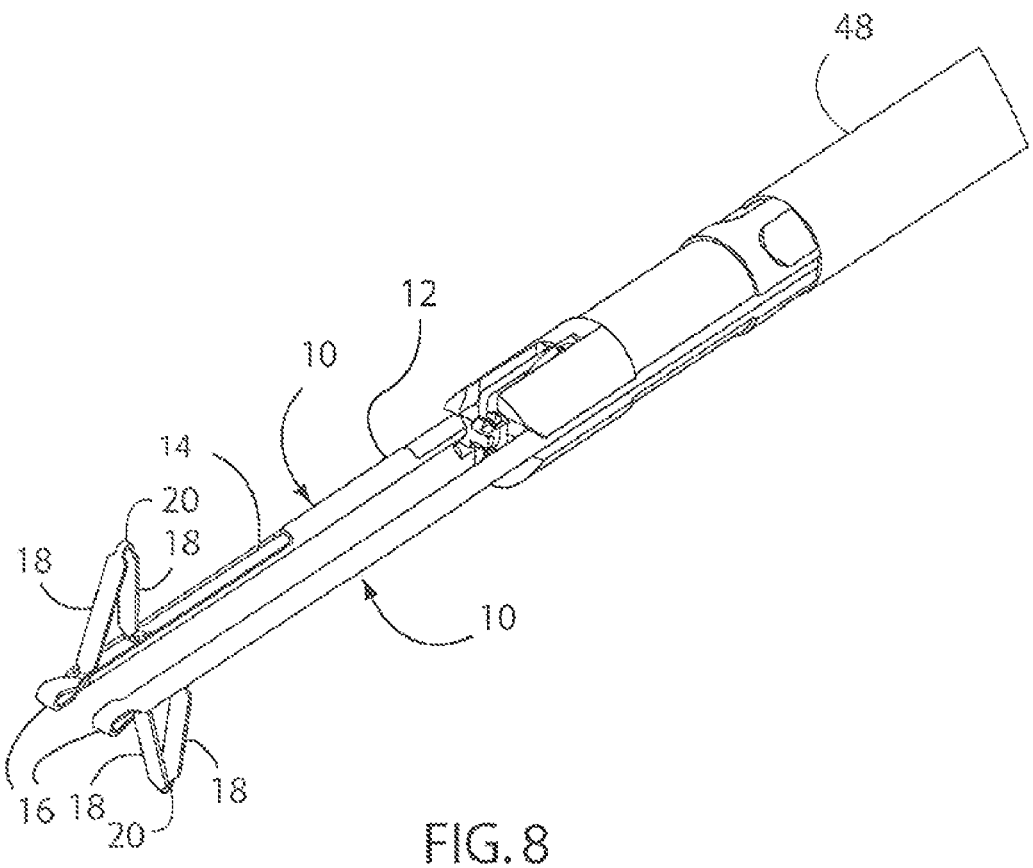
FIG. 8 is a perspective view of the end effector having butterfly members in a second, expanded configuration.

After the end effector 4 is in the standby position, at least one butterfly member 10 is actuated to move from its first, collapsed configuration to its second, expanded configuration. This actuation may be performed in any suitable manner. Referring also to FIG. 8, as one example, the second element 14 of each butterfly member 10 is held substantially in place, and the first element 12 of each butterfly member 10 is pulled proximally in any suitable manner. As one example, the elements 12, 14 each extend through the shaft 6 to the handle 8, and a mechanism or mechanisms in the handle 8 push or otherwise move the first element 12 proximally. As another example, the first element 12 is connected to a cable or other force transmission member, and the handle 8 exerts a proximal force on that cable, which in turn moves the first element 12 proximally.

Proximal motion of the first element 12 relative to the second element 14 exerts a compressive force on the segments 18, substantially in the longitudinal direction. Because at least one segment 18 is angled, curved or otherwise offset from the longitudinal direction, that longitudinal force results in a moment that acts on at least part of at least one segment 18. As a result of that moment, each segment 18 rotates outward from the longitudinal centerline of the first element 12 about the hinge member 20 as well as about the point of connection between each segment 18 and a remainder of the first element 12. The hinge member 20 allows the segments 18 to rotate relative to one another at a defined point, by providing a weakened area or other feature that is configured to bend upon the application of a force that is less than the amount of force needed to bend the segments 18 themselves. The deflection of the segments 18 as a result of the application of moments thereto may be plastic deformation. Alternately, that deflection may be elastic deformation. After the segments 18 of a butterfly member 10 complete their deflection, that butterfly member 10 is in the second, expanded configuration. Alternately, the segments 18 are bendable, rather than deformable. Alternately, a single segment 18, rather than two separate segments, is provided. As another example, the first element 12 of each butterfly member 10 is held substantially in place, and the second element 14 of each butterfly member 10 is pushed distally, such as by a rod or other rigid linkage attached to the end of each second element 14. This motion of the second element 14 relative to the first element 12 exerts a compressive force on the segments 18, which then deform to the second, expanded configuration substantially as described above.

Figure 8A:
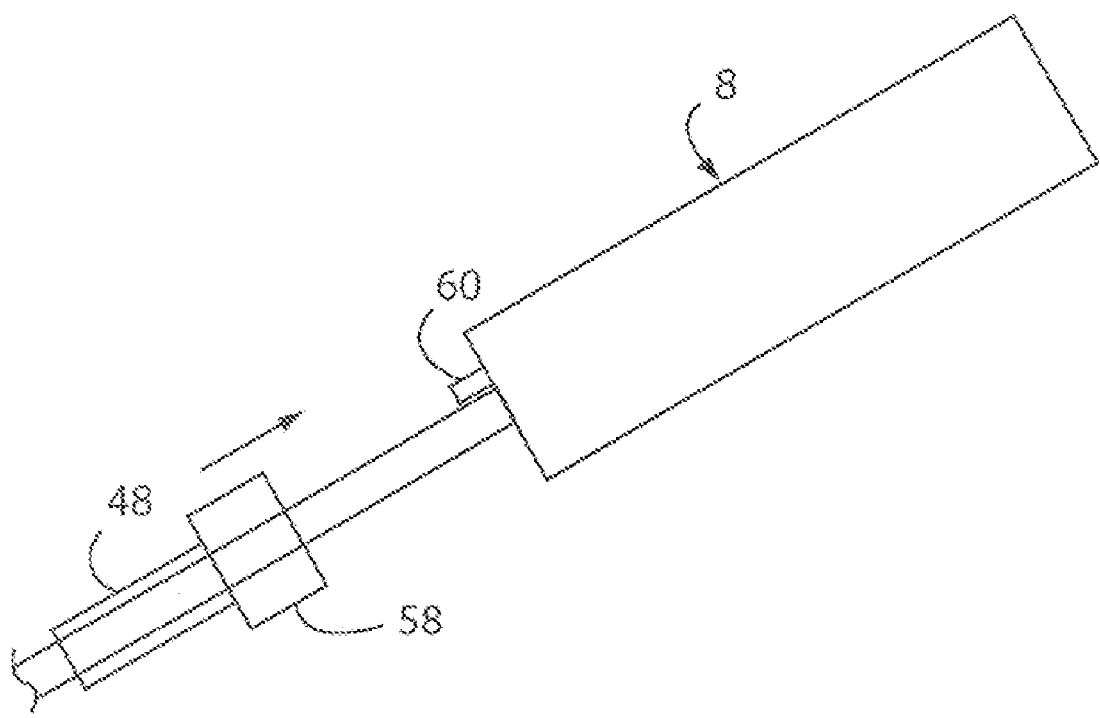
FIG. 8A is a schematic view of the handle and shaft of the vascular closure system and their relationship with a sheath.
Figure 16:
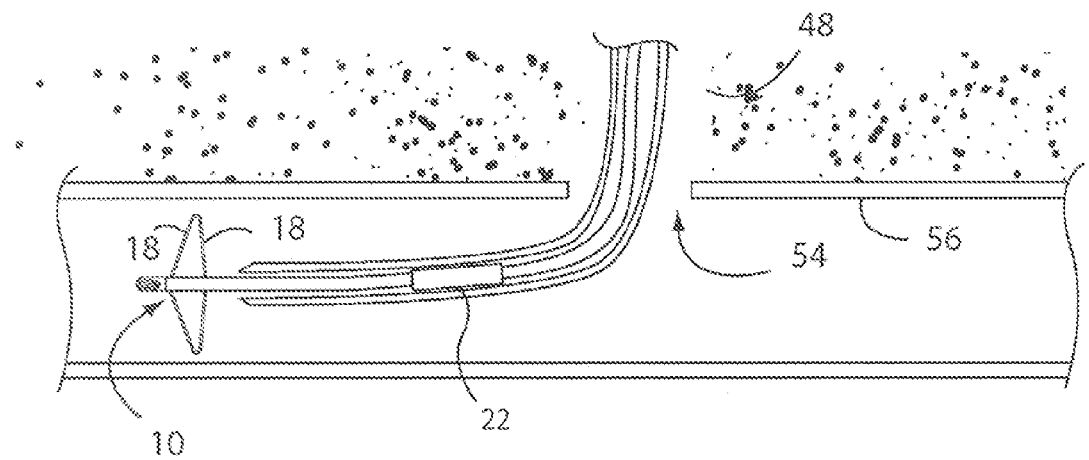
FIG. 16 is a side view of a third step in the operation of the closure system.

The sheath 48 may be removed from the tissue 52 of the patient prior to the expansion of at least one butterfly member 10. Referring also to FIG. 16, the closure system 2 may be configured such that removal of the sheath 48 from the tissue of the patient causes or allows expansion of at least one butterfly member 10. For example, referring also to FIG. 8A, the sheath 48 may include or be connected to a ring 58 or other structure at its proximal end. The handle 8 may include a button 60 at its distal end. The shaft 6 is positioned within the lumen of the sheath 48. As the sheath 48 is slid proximally out of the tissue 52 of the patient along the shaft 6, the ring 58 contacts the button 60, moving it from a first position to a second position. This motion of the button 60 may actuate a mechanism or mechanisms within the handle 8 to allow at least one butterfly member 10 to move to an expanded configuration and/or to cause at least one butterfly member 10 to move to an expanded configuration. Each butterfly member 10 in the expanded configuration is located within the lumen of the blood vessel 56. Alternately, the sheath 48 remains in place as at least one butterfly member 10 moves to the expanded configuration. Alternately, the actuation of at least one butterfly member 10 to move to the expanded configuration may be completely independent of the position of the sheath 48 relative to the handle 8 or any other component of the closure system 2.

Figure 17:
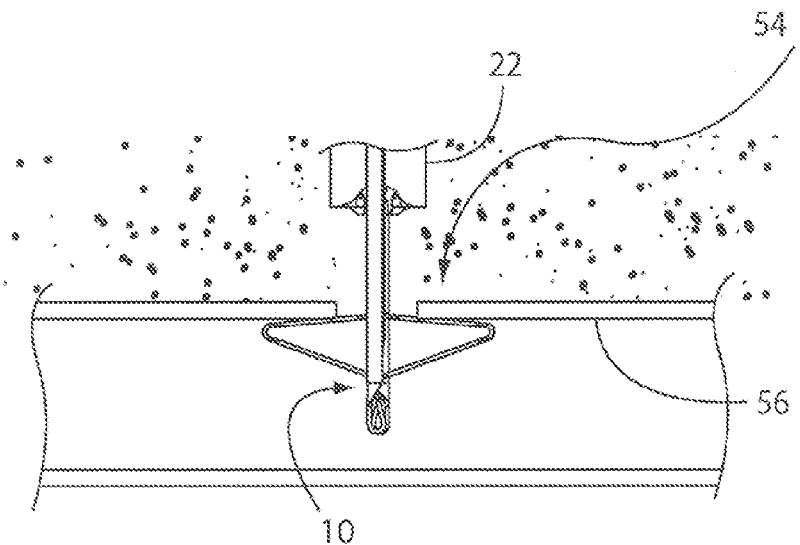
FIG. 17 is a side view of a fourth step in the operation of the closure system.

Next, referring also to FIG. 17, the closure system 2 is moved proximally until the expanded butterfly member or members 10 contact the inner wall of the blood vessel 56, in proximity to the opening 54. The butterfly members 10 are held substantially stationary relative to the housing 22 as the closure system 2 is moved proximally. The closure system 2 may be moved proximally in any suitable manner. As one example, the handle 8 is manually moved proximally, causing the expanded butterfly member or members 10 to contact the inner wall of the blood vessel 56. When the closure system 2 reaches the position in which a segment 18 of each expanded butterfly member 10 contacts the inner wall of the blood vessel 56, the blood leakage indicator or indicators 50 have moved out of the lumen of the blood vessel 56 through the opening 54, and into the passage 53 in the tissue 52. As a result, the flow of blood through the blood leakage indicator or indicators 50 decreases or stops, indicating to the operator that the butterfly member or members 10 are positioned against the inner surface of the wall of the blood vessel 56.

Figure 9:
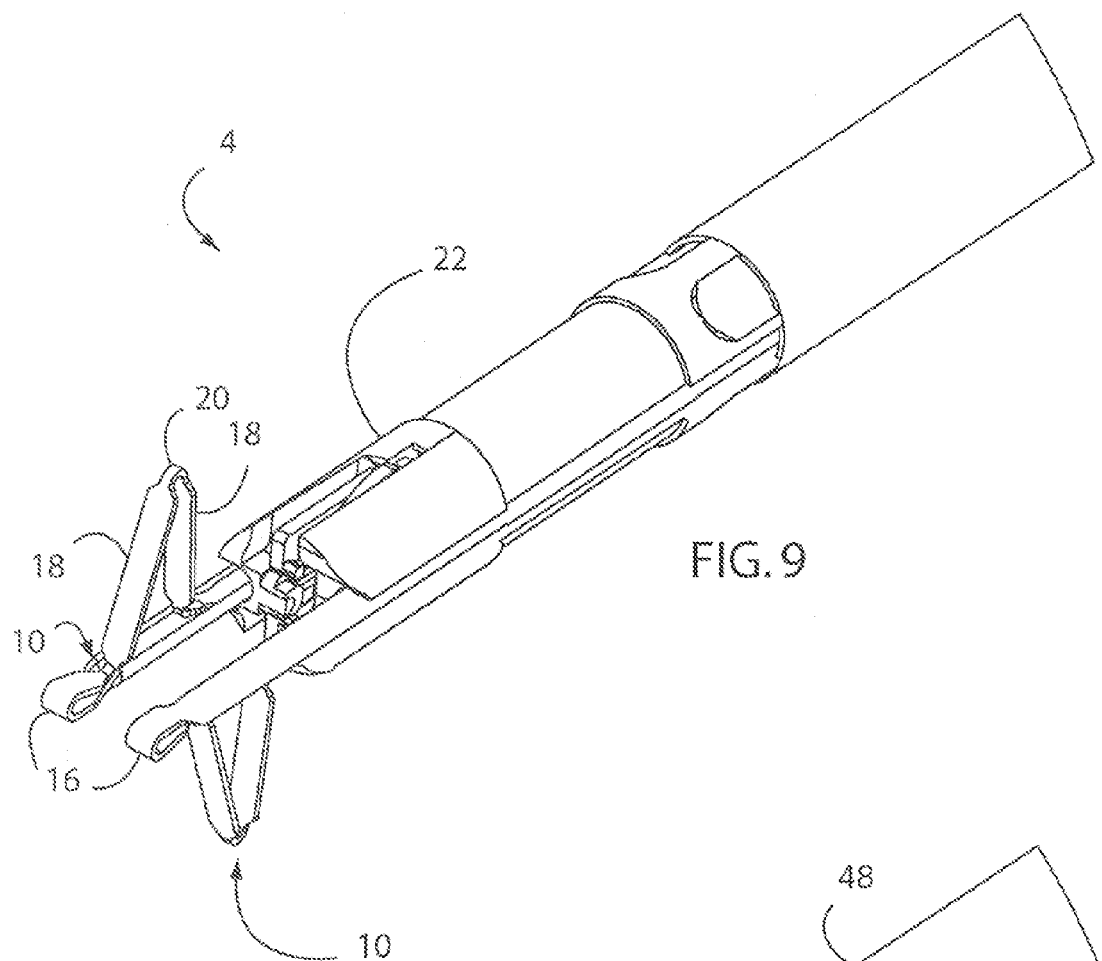
FIG. 9 is a perspective view of the end effector after the butterfly members have been moved proximally.
Figure 18:
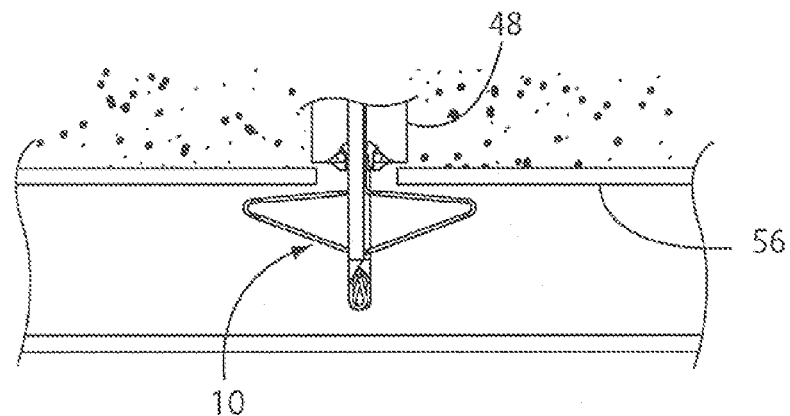
FIG. 18 is a side view of a fifth step in the operation of the closure system.

Referring also to FIGS. 9 and 18, each butterfly member 10 is then moved proximally while the housing 22 is held in a substantially constant position. The butterfly members 10 are moved such that each butterfly member 10 is maintained in an expanded configuration as it moves proximally. As a result, the expanded portion of each butterfly member 10 pulls the wall of the blood vessel 56 toward the distal end of the housing 22, capturing the wall of the blood vessel 56 and registering the opening 54 in the blood vessel 56 to the distal end of the housing 22. The expanded portion of each butterfly member 10 may be wider than the opening 54 to facilitate this motion of the wall of the blood vessel 56. Advantageously, the expanded portion of each butterfly member 10 may be moved within one-half millimeter of the distal end of the housing 22. However, the distance that the expanded portion of each butterfly member 10 is moved may be more or less. Alternately, at least one butterfly member 10 is moved relative to a force, rather than a distance. That is, a particular force is exerted proximally on the butterfly member 10, causing it to move proximally until the force exerted on the butterfly member 10 by the wall of the blood vessel 56 in the distal direction is substantially equal to the force exerted on the butterfly member 10 in the proximal direction. Thus, the wall of the blood vessel 56 is moved into position in preparation for stapling. The wall of the blood vessel 56 is held in position against the distal end of the housing by compressive force exerted against the housing 22 by the expanded portion of each butterfly member 10. The movement of each butterfly member 10 may be accomplished in any suitable manner. For example, at least one element 12, 14 of at least one butterfly member 10 extends to the handle 8, and at least one of those elements 12, 14 is actuated directly by a mechanism or mechanisms associated with the handle 8. As another example, both the first and the second elements 12, 14 of at least one butterfly member 10 may be moved proximally by a cable or cables attached to the elements 12, 14. Alternately, the expanded portion of each butterfly member 10 is held substantially stationary, and the housing 22 is advanced distally. Such motion of the housing 22 may be accomplished in a manner similar to that described above with regard to the motion of the butterfly members 10. For example, each butterfly member 10 may be held substantially stationary relative to the handle 8, which in turn is held substantially stationary relative to the blood vessel 56. A force in the proximal direction is then exerted on the housing 22, such as via a member capable of transmitting compressive force, where that member extends through the shaft 6 to the handle 8.

Next, referring also to FIG. 10, the driver 34 advances distally. The driver 34 may be actuated to advance distally in any suitable manner. As one example, the driver 34 is urged distally when the handle 8 exerts a distal force on a member (not shown) or other structure or mechanism connected to the driver 34. The handle 8 may exert such a force in any suitable manner, as described above. As another example, the driver 34 extends through the shaft 6 to the handle 8, and the driver 34 is actuated directly by a mechanism or mechanisms associated with the handle 8. As another example, a cable is connected to the driver 34, and that cable is directed around a nose, axle or other feature (not shown) of the end effector 4 distal to the driver 34 in order to convert proximal motion of the cable to distal motion of the driver 34.

As the driver 34 advances distally, the driver 34 exerts a force in the distal direction on the staple 24. Each ridge 41 restrains the corresponding valley 29 of the staple 24 substantially against distal motion, such that the longitudinal position of the peaks 28 and the trough 30 of the staple are substantially unchanged as the driver 34 begins to exert a distal force on the staple 24. However, the tines 26 are not substantially restrained against motion resulting from application of force in the distal direction. The distal force exerted on at least one peak 28 of the staple 24 by the driver 34 urges each valley 29 of the staple 24 against the corresponding ridge 41 of the paddle 40. Each ridge 41 is positioned sufficiently far from the longitudinal centerline of the staple 24 such that a moment is generated about that ridge 41 that is applied to the corresponding peak 28 of the staple 24. This moment causes the corresponding tine 26 of the staple 24 to move outward from the longitudinal centerline of the staple 24. Each ridge 41 may be shaped, sized, positioned or otherwise configured in any manner that results in such a moment and the resultant motion of the tines 26 of the staple 24.

Thus, as the driver 34 exerts a force on the staple 24, the distal ends of the tines 26 of the staple 24 move apart from one another, each in a direction away from the longitudinal centerline of the staple 24. This deformation of the staple may be referred to as "splaying." During splaying of the staple 24, the tines 26 themselves may remain substantially undeformed; rather, a portion of the staple 24 in proximity to each peak 28 and/or the trough 30 may deform. Alternately, at least one tine 26 may deform during splaying of the staple 24. Further, as the distal ends of the tines 26 move away from the longitudinal centerline of the staple 24, at least part of each tine 26 may move outside the distal end of the housing 22 through a slot 23 or other opening in the housing 22. As a result, the tines 26 of the staple 24 may move apart from one another a distance greater than the diameter of the housing 22. Where the staple 24 is made from a plastically-deformable material such as stainless steel, the staple 24 deforms plastically as it splays from its initial configuration to the splayed configuration. Plastic deformation is deformation that remains after the load that caused it is removed, or that would remain if the load were removed. Alternately, the staple 24 is elastically-deformable from its initial configuration to the splayed configuration. The staple 24 may be spring-loaded inwards to the initial configuration, such that the staple 24 springs outward and returns to the splayed configuration upon application of force or upon movement to a position relative to the housing 22 such that the staple 24 is free to spring outward. Alternately, the staple 24 does not deform or move to a splayed configuration at all; rather, it transitions directly from the initial configuration to a closed configuration as described below. If the staple 24 does not deform or move to a splayed configuration, then the tines 26 may be spaced apart as far as possible within the housing 22 when the staple 24 is in the initial configuration, such that the tines 26 are farther apart from one another than shown in FIG. 5.

Alternately, where at least one paddle 40 is angled or curved relative to the driver 34 as described above, as each tine 26 moves its inner surface 27 contacts an outer edge of the paddle 40. Such contact between each tine 26 and the corresponding paddle 40 causes the staple 24 to splay. That is, at least one tine 26 of the staple 24 moves away from the longitudinal centerline of the staple 24.

After the staple 24 has deformed to a splayed configuration, as shown in FIG. 10, the driver 34 continues to apply a force in the distal direction on the staple 24. This force pushes the splayed staple 24 at least partially onto each ridge 41, in turn causing the paddle 40 associated with each ridge 41 to deflect away from the longitudinal centerline of the driver 34, which at this point in the operation of the closure system 2 is substantially coaxial with the longitudinal centerline of the staple 24. The staple 24 then moves distal to the ridge or ridges 41. As the staple 24 moves distally, the driver 34 encounters each ridge 41. Contact between the driver 34 and each ridge 41 holds each paddle 40 in a position deflected away from the longitudinal centerline of the driver 34. After the staple 24 has moved distally to the ridge or ridges 41, it may advance rapidly toward the distal end of the housing 22, as the portion of the paddle 40 distal to each ridge 41 is out of the path of travel of the staple 24. Further, as the staple 24 advances, the tab 32 in the staple 24 slides along a substantially longitudinal groove 47 defined in the finger 42. The groove 47 may extend completely through the finger 42, or may be a depression defined in the finger 42. The tab 32 may extend into the groove 47 of the finger 42. Interaction between the tab 32 of the staple 24 and the groove 47 may maintain the staple 24 in a desired orientation during its splaying, shuttling forward, closing and/or ejecting. Alternately, the tab 32 and/or a different registration element of the staple 24 rides along a corresponding registration element defined in the housing 22. The motion of the staple 24 between its splaying and the entry of the tines 26 into tissue 56 may be referred to as "shuttling." During shuttling, the compressive force that deformed the staple 24 into the splayed configuration is substantially removed from the staple 24, because the staple 24 is free to move forward; the force exerted by the driver 34 on the staple 24 moves it distally rather than further deforming it.

Figure 10A:
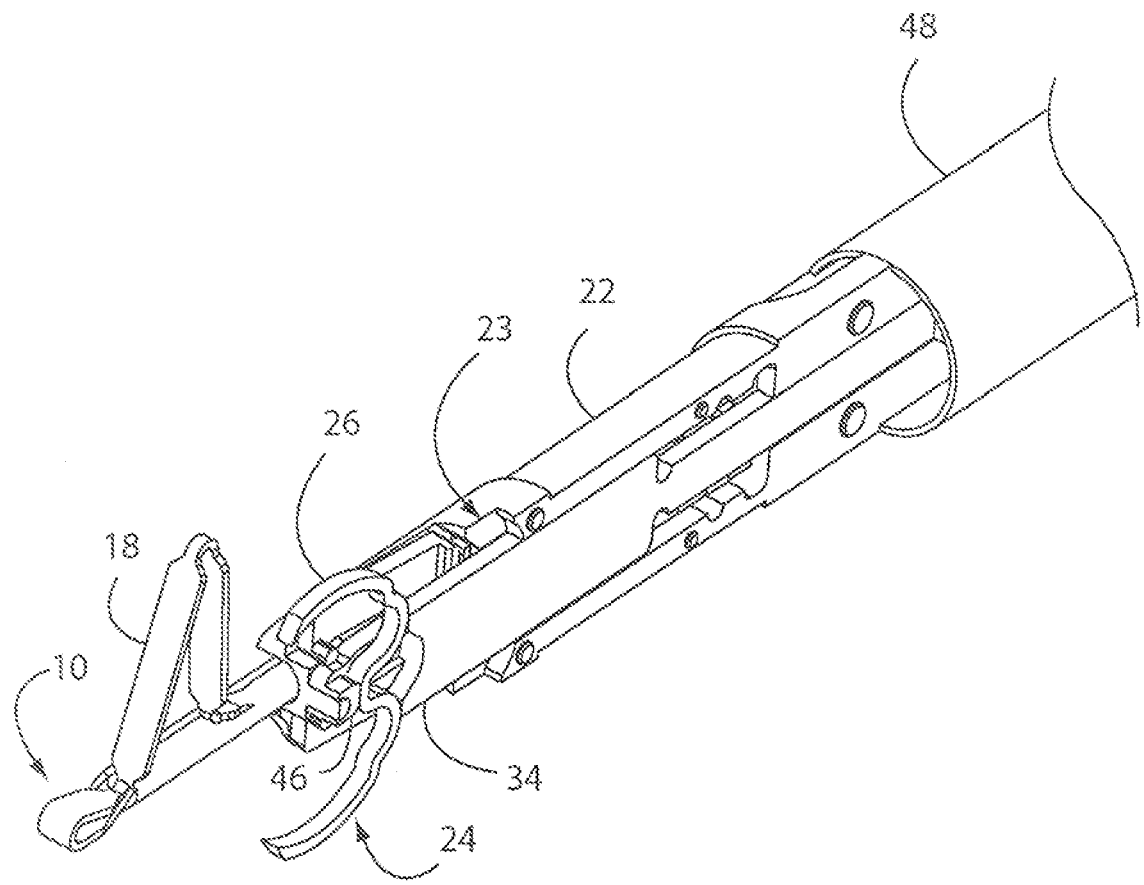
FIG. 10A is a perspective view of the end effector in a third configuration, after the splayed staple has been shuttled distally.

Referring also to FIGS. 7 and 10A, as the driver 34 continues to move distally, it pushes the distal ends of the tines 26 out of the distal end of the housing 22, and the distal ends of the tines 26 then penetrate the wall of the blood vessel 56. The speed of the shuttling of the staple 24 may be controlled to facilitate penetration of the wall of the blood vessel 56. The staple 24 is in the splayed configuration as the distal ends of the tines 26 penetrate the wall of the blood vessel 56. The distal ends of the tines 26 are positioned further apart from one another when the staple 24 is in the splayed configuration than when the staple 24 is in the initial configuration, thereby allowing capture of tissue across a width greater than that of the housing 22 between the tines 26 as they enter and penetrate tissue 56. The staple 24 in the splayed configuration penetrates tissue 56 on opposite sides of the opening 54. The staple 24 may be positioned substantially across the center of the opening 54. Alternately, more than one staple 24 is deployed to close the opening 54.

As the driver 34 continues to move distally, it continues to move the staple 24 distally. As the staple 24 moves distally, the trough 30 of the staple encounters the projection 46 that extends from the finger 42. The projection 46 is positioned in the path of the staple 24 in order to contact the trough 30 of the staple 24 as it moves distally. That contact causes distal motion of the staple 24 to substantially stop. However, the driver 34 continues to exert a force in the distal direction on the staple 24, such as on the peaks 28 of the staple 24.

After the staple 24 substantially ceases its distal motion, the driver 34 continues to apply a distal force to the staple 24. Each peak 28 of the staple 24 is offset from the longitudinal centerline of the staple 24. Further, the longitudinal centerline of the staple 24 substantially intersects or approaches close to intersection with the projection 46. As a result, each peak 28 of the staple 24 is offset from the projection. The force exerted by the driver 34 distally on each peak 28 of the staple 24, which is offset from the longitudinal centerline of the staple 24, results in a moment about the projection 46, which acts as an anvil. Each tine 26 of the staple 24 that experiences that moment moves toward the longitudinal centerline of the staple 24. In the course of this motion, the distal ends of the tines 26 may first move toward the longitudinal centerline of the staple 24 and toward one another, cross each other, then move away from the longitudinal centerline of the staple 24 and away from one another. The tines 26 need not substantially change shape as they move; rather, they may rotate about a pivot point located at or near the trough 30. Alternately, one or both of the tines 26 may deform as they move. The radius of curvature of each tine 26 may be substantially coincident with its path of travel during closure of the staple 24. Deformation of the staple 24 as a result of contact between the staple 24 and the projection 46 may be referred to as "closing" the staple 24.

Figure 11:
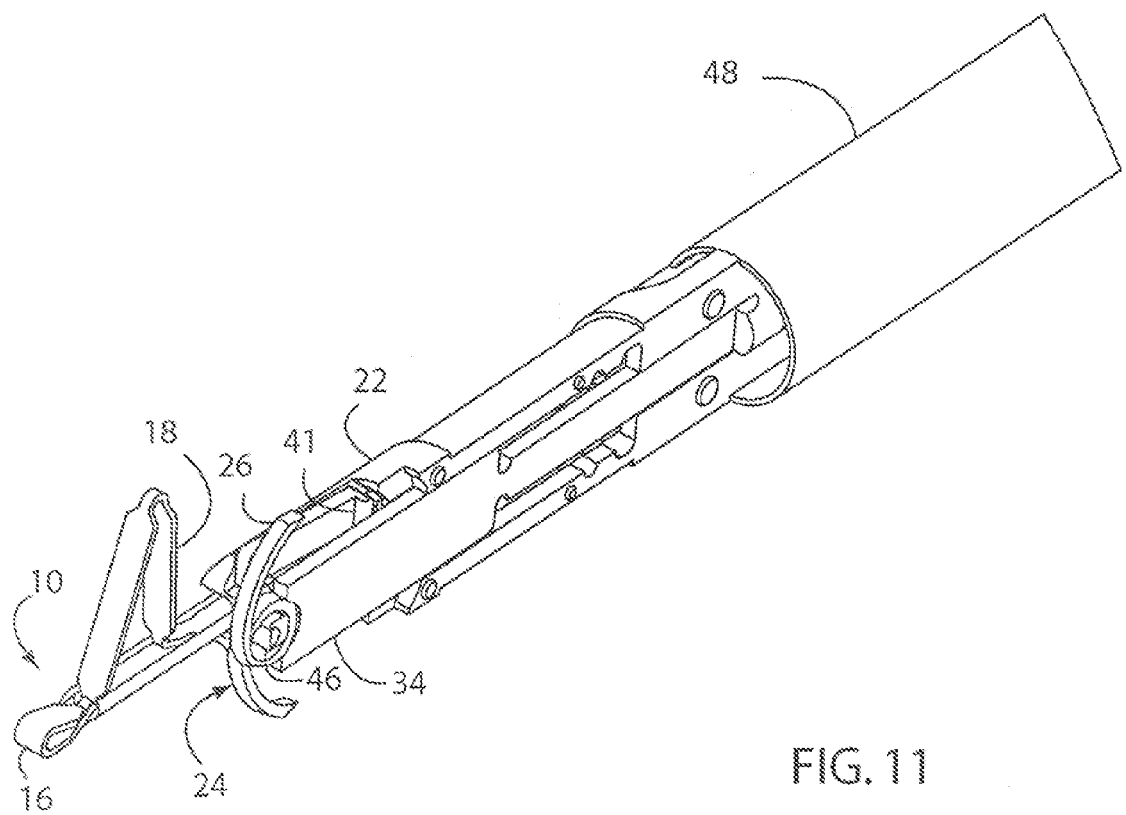
FIG. 11 is a perspective view of the end effector in a fourth configuration, as the staple is closed.

Referring also to FIG. 11, as the driver 34 continues to move distally, the staple 24 continues to deform against the projection 46. This deformation may be plastic deformation from the splayed configuration to a final, closed configuration. The staple 24 and/or any other component of the end effector 4 may be shaped or otherwise configured such that the tines 26 swipe past one another as the staple 24 moves to the closed configuration. Referring also to FIG. 12, as one example, the staple 24 is shaped such that the application of force longitudinally thereto causes the tines 26 to move in a direction that has a component of motion perpendicular to the longitudinal direction, thereby moving the tines 26 such that they swipe past each other. The staple 24 may be curved in any manner to allow for such motion of the tines 26. For example, the proximal surface 62 of the staple 24 may take the shape of a twisted plane, as described above. Contact between the driver 34 and the proximal surface 62 of the staple thus causes the tines 26 to move apart from one another in a direction perpendicular to the direction in which the legs move toward one another as the staple 24 moves to a closed configuration, such that the tines 26 swipe past one another as the staple 24 closes. That is, because the force applied to the proximal surface 62 of the staple 24 is substantially in the longitudinal direction, and the proximal surface 62 of the staple 24 is twisted such that lines perpendicular to that proximal surface 62 on opposite lateral sides of the staple 24 are skewed in opposite directions relative to the longitudinal direction, the force applied to the staple 24 tilts the tines 26 in opposite directions. Thus, when the staple 24 is closed, the tines 26 may be both offset from and substantially adjacent to one another. Alternately, at least two tines 26 of the staple 24 are configured to interfere with or otherwise engage one another when the staple 24 is in the closed position. Alternately, at least two tines 26 may be substantially parallel to one another and spaced apart from one another when the staple 24 is in the closed position.

Alternately, the distal ends of the tines 26 of the staple 24 are shaped substantially conically. As the staple 24 closes, the conical tips of the tines 26 come into contact with one another. As a result of the angle of the side of each conical tip, this contact causes the tines 26 to slide adjacent to one another instead of interfering with one another. Alternately, the distal end of each tine 26 is substantially planar, where each plane is oriented in a different direction. As a result, when the distal ends of the tines 26 encounter one another, contact between the differently-oriented planes at the distal ends of the tines pushes the tines 26 out of plane relative to one another. Alternately, the tines 26 of the staple 24 are fabricated such that they are out of plane with one another when the staple 24 is in the initial configuration, such that the tines 26 do not substantially interfere with one another during deployment. Alternately, the tines 26 of the staple 24 are plastically deformed out of plane with one another by contact with the paddle 40 while the staple 24 is splayed open and/or being closed. Alternately, the staple 24 and/or the end effector 4 are configured to prevent the tines 26 from interfering with one another as the staple 24 closes.

When deformation of the tines 26 of the staple is complete, the staple 24 is in the closed configuration. In that closed configuration, at least part of each tine 26 of the staple is located within the lumen of the blood vessel 56. The tines 26 may be positioned such that a part of each tine 26 is positioned against an inner surface of the blood vessel 56. Alternately, the tines 26 may be positioned differently relative to the wall of the blood vessel 56. In the closed configuration, the staple 24 holds opposite sides of the opening 54 together, substantially closing the opening 54. Where the staple 24 is frangibly connected to the driver 34, force is exerted on the staple 24 when the staple 24 approaches or reaches the closed configuration, in order to separate the staple 24 from the driver 34 such as by fracturing. The force on the staple 24 may be provided in any suitable manner. As one example, the connection between the staple 24 and the driver 34 may be shaped and sized such that the forces exerted on the staple 24 to deform it to the closed configuration also cause the staple 24 to separate from the driver 34. Alternately, the staple 24 is not separated from the driver 34 until the staple 24 is ejected from the housing 22. Alternately, the staple 24 is separated from the driver 34 at any other suitable time during the deployment process.

In the course of deflecting the staple 24 to the closed configuration, the driver 34 moves to a distalmost position. The distalmost position of the driver 34 may be controlled in any suitable manner. As one example, the distalmost position of the driver 34 is controlled by the handle 8. As another example, contact between the distal end of the driver 34 and at least one post 43 extending from a corresponding paddle 40 prevents the driver 34 from moving further in the distal direction, thereby defining the distalmost position of the driver 34.

After the staple 24 has been closed, the driver 34 is moved proximally. As the driver 34 moves proximally, it continues to engage at least one ridge 41 extending from each paddle 40, such that the paddles 40 continue to be deflected away from their original, rest position. As the driver 34 continues to move proximally, the distal end of the driver 34 moves over and then proximal to each ridge 41. After the distal end of the driver 34 has moved proximal to each ridge 41, the driver 34 no longer pushes the corresponding paddle 40 from its original position. Consequently, each paddle 40 moves back toward its original position. Advantageously, the deflection of each paddle 40 away from its original position is substantially elastic, such that in the deflected position each paddle 40 is biased toward its initial position. Alternately, at least one paddle 40 is plastically deformed away from its original position as the driver 34 moves distally, and each such paddle 40 does not return to its original position when the distal end of the driver 34 moves proximal to the corresponding ridge 41. If so, when the driver 34 retracts proximally, a feature on the driver 34 and/or a separate member (not shown) plastically deform the paddle 40 back toward its initial position in order to eject the staple, as described below. Alternately, at least one paddle 40 is not deflectable from a cantilevered base, but instead is movable relative to the housing 22 in any suitable direction.

As each paddle 40 moves back toward its original position, it exerts a force on the closed staple 24 along the projection 46, urging the staple 24 along the projection 46 away from the finger 42 and toward the free end of the projection 46. When each paddle 40 moves close to or completely into its initial position, it has moved far enough to push the closed staple 24 off the free end of the projection 46. The closed staple 24 is then free to exit the housing 22 of the end effector 4.

Next, each butterfly member 10 is deformed from the expanded configuration back to the collapsed configuration. This deformation may be performed by reversing the steps described above for deforming the butterfly member 10 from the collapsed configuration to the expanded configuration. Where at least one butterfly member 10 elastically deformed from the collapsed configuration to the expanded configuration, force exerted on that butterfly member 10 to maintain the butterfly member in the expanded configuration is simply released, allowing the butterfly member 10 to return to the collapsed configuration.

After each butterfly member 10 returns to the collapsed position, the end effector 4 is moved proximally, and the butterfly members 10 then exit from the opening 54. Advantageously, where two butterfly members 10 are used, one butterfly member 10 is located on each side of the closed staple 24. As the end effector 4 is moved away from the opening 54, the staple 24 exits the distal end of the housing 22, as it grasps the tissue 56 with greater force than any remaining frictional forces or other incidental forces holding it to the housing 22. The guidewire, if used, is then removed from the blood vessel 56. Alternately, the guidewire is removed at a different time. The guidewire is pulled out of the blood vessel 56 adjacent to the closed staple 24 and between the edges of what had been the opening 54 in the blood vessel 56. Thus, a smaller-diameter guidewire may be advantageous, as it may leave a smaller gap in tissue between the edges of what had been the opening 54 in the blood vessel, such that the wall of the blood vessel can rebound more quickly to close that gap. After the end effector 4 is removed from the patient, the sheath 48 is removed if it is still present in the patient. The procedure is complete, and the opening 54 is substantially closed.

Where the closure system 2 includes a separate butterfly deployment tool connected to and configured to place the butterfly members 10, and a separate staple placement tool which is connected to the end effector 4 and configured to place the staple 24, each of the two separate components is substantially as described above with regard to the single, integrated tool, with minor variations. First, the butterfly deployment tool is inserted through the opening 54 in the blood vessel 56 and actuated such that a part of each butterfly member 10 is in the expanded configuration and seated against the inner surface of the wall of the blood vessel 56. Then, the staple placement tool is slid along the butterfly deployment tool toward the opening 54 in any suitable manner, and actuated substantially as described above. The staple placement tool is then withdrawn. Optionally, a second staple placement tool then may be advanced toward the opening 56 and actuated. The second staple placement tool may be used in the event that the first staple placement tool did not close the opening 56 to the satisfaction of the physician, in order to place a second staple for additional security, or for any other reason. After the staple placement tool is withdrawn, the butterfly deployment tool is withdrawn, the opening 56 is substantially closed, and the procedure is complete.

While the invention has been described in detail, it will be apparent to one skilled in the art that various changes and modifications can be made and equivalents employed, without departing from the present invention. It is to be understood that the invention is not limited to the details of construction, the arrangements of components and/or the details of operation set forth in the above description or illustrated in the drawings. Headings and subheadings are for the convenience of the reader only. They should not and cannot be construed to have any substantive significance, meaning or interpretation, and should not and cannot be deemed to be limiting in any way, or indicate that all of the information relating to any particular topic is to be found under or limited to any particular heading or subheading. The contents of each section of this document are merely exemplary and do not limit the scope of the invention or the interpretation of the claims. Therefore, the invention is not to be restricted or limited except in accordance with the following claims and their legal equivalents.

What is claimed is:

1. A method for closing an opening in tissue, comprising:
providing a staple having a plurality of tines and a longitudinal centerline, wherein said staple is a substantially continuous solid;
plastically deforming said staple to a splayed configuration;
penetrating at least one said tine into tissue in proximity to the opening;
plastically deforming said staple to a closed configuration; and
pushing said staple in a direction transverse to said longitudinal centerline after said plastically deforming said staple to a closed configuration, whereby said pushing releases said staple.

2. The method of claim 1, wherein said plastically deforming said staple to a closed configuration includes deforming at least one said tine to a position offset from and substantially adjacent to another said tine.

3. The method of claim 1, further comprising
providing a housing; and
holding said staple at least partially within said housing.

4. The method of claim 3, wherein said holding comprises holding said staple at a location spaced apart from the distal end of said housing.

5. The method of claim 3, wherein said holding comprises holding said staple completely within said housing at a location spaced apart from the distal end of said housing before said plastically deforming said staple to a splayed configuration.

6. The method of claim 3, further comprising registering the opening in tissue to said housing.

7. The method of claim 6, wherein said registering includes maintaining said housing substantially stationary; and
moving the tissue toward said housing.

8. The method of claim 6, wherein said registering includes:
providing at least one butterfly member extending substantially distally from said housing;
inserting at least part of at least one said butterfly member into the opening in a collapsed configuration;
expanding at least part of at least one said butterfly member to an expanded configuration; and
moving at least one of said butterfly member in said expanded configuration and said housing toward the other.

9. The method of claim 8, further comprising:
collapsing each said butterfly member in said expanded configuration to said collapsed configuration; and
withdrawing each said butterfly member from the opening.

10. The method of claim 1, wherein said direction is substantially perpendicular to said longitudinal centerline.

11. The method of claim 1, wherein said staple has two tines and lies substantially in a single plane.

12. A method for closing an opening in tissue, comprising:
providing a staple having a plurality of tines, and a paddle including a ridge defined thereon, said ridge positioned between said tines;
plastically deforming said staple to a splayed configuration by applying force in the distal direction against a proximal surface of said staple, wherein said plastically deforming said staple to a splayed configuration includes moving said staple and said ridge into contact with one another to generate a moment about said ridge that results in motion of said tines;
penetrating at least one said tine into tissue in proximity to the opening; and
plastically deforming said staple from said splayed configuration to a closed configuration by applying force in the distal direction against a proximal surface of said staple.

13. The method of claim 12, wherein said staple has two tines and lies substantially in a single plane; further comprising moving said ridge substantially perpendicularly out of said plane after said plastically deforming said staple from said splayed configuration to a closed configuration.

14. The method of claim 12, wherein said plastically deforming said staple to said closed configuration includes moving an outer surface of said staple into contact with a projection oriented at a angle to the direction of said moving, said contact restraining said staple against distal motion.

15. The method of claim 14, further comprising urging said staple in said closed configuration along and then off of said projection.

* * * * *